United States Patent [19]
Tarr

[11] Patent Number: 5,824,556
[45] Date of Patent: Oct. 20, 1998

[54] PEPTIDE MASS LADDERS GENERATED USING CARBON DISULFIDE

[76] Inventor: George E. Tarr, 640 Essex St., So. Hamilton, Mass. 01982

[21] Appl. No.: 872,888

[22] Filed: Jun. 11, 1997

[51] Int. Cl.$^6$ .................................................. G01N 33/00
[52] U.S. Cl. .............................. 436/89; 436/86; 436/173; 530/345
[58] Field of Search .................................. 260/8; 436/89, 436/86, 173; 530/345

[56] References Cited

U.S. PATENT DOCUMENTS

| | | | |
|---|---|---|---|
| 4,065,412 | 12/1977 | Dreyer | 260/8 |
| 5,246,865 | 9/1993 | Stolowitz | 436/89 |
| 5,250,664 | 10/1993 | Fromont | 530/377 |
| 5,470,753 | 11/1995 | Sepetov | 436/89 |
| 5,521,097 | 5/1996 | Uchida | 436/86 |
| 5,538,897 | 7/1996 | Yates | 436/89 |

*Primary Examiner*—Cecilia J. Tsang
*Assistant Examiner*—David Lukton

[57] ABSTRACT

A method for chemically generating a set of N-terminally truncated peptides (ladder), suitable for analysis by mass spectrometry (MS), from a peptide or protein using carbon disulfide ($CS_2$). The method consists of: 1) a coupling step employing $CS_2$, a tert-amine catalyst, and a solvent under conditions that maximize the yield of dithiocarbamyl-peptide, and 2) a cleavage step employing an acid, which catalyzes two alternate pathways, removal of the N-terminal residue and regeneration of the starting peptide, with no other modification. The simultaneous operation of both pathways generates a ladder without further intervention. This pair of steps may be repeated a controlled but unlimited number of times with drying between each step in order to generate a ladder of any desired length. Finally, the processed peptide is analyzed by MS, wherein the sequence of the peptide is deduced from the mass ladder. The ratio of cleavage to regeneration permits the distinction of isoleucine and leucine.

1 Claim, 5 Drawing Sheets

PEPTIDE MASS LADDERS GENERATED USING CARBON DISULFIDE

BACKGROUND

1. Field of Invention

This invention relates to chemical processing of peptides and proteins for analysis by mass spectrometry, specifically to a novel method for generating a nested set of N-terminally truncated peptides (mass ladders) from a starting peptide.

2. Discussion of Prior Art

The traditional approach to protein structural chemistry, comprised mostly of intensive chromatographic (HPLC) and electrophoretic separations and Edman sequencing, is being supplemented or displaced by methods tied to mass spectrometry (MS). The poor sensitivity, labor and slow analyses of the traditional approach are much alleviated by high throughput MS using the gentle ionization techniques of matrix-assisted laser desorption ionization (MALDI) and electrospray ionization (ESI) coupled to various mass analyzers, such as quadrapole, time-of-flight (TOF), and ion-trap. Yet, powerful as simple, accurate mass analysis of a single protein/peptide or the components of mixtures (e.g., a proteolytic digest) has proven to be, there is a pressing need for methods of deriving more detailed information from these components. In the absence of convenient and effective chemistry for specific sample modification, mass spectrometrists have had to rely on analysis of gas-phase decompositions (e.g., post-source decay, collision-induced dissociation), but these processes are highly sequence dependent, therefore erratic and generally an interpretive nightmare.

An alternative is to use wet chemistry. The specific processing that generates the most definitive information is amino acid sequencing, classically with the standard Edman chemistry using phenylisothiocyanate (PITC) wherein cyclical control of reagents and pH allows a stepwise removal of amino acids from the N-terminus of a peptide or protein[1]. There are two fundamentally different ways of extracting sequence information from this process, the first being to analyze the amino acid derivative released. All current protein sequencing instruments (which are based on the "gas-phase" sequencer[2]) utilize this strategy, and all employ reversed-phase high performance liquid chromatography (RP-HPLC) to separate and quantitatively detect the various phenylthiohydantoin amino acids (PTH's), the PTH being the more stable isomeric form of the released amino acid. Some marginal improvement in this approach could be achieved by replacing HPLC analysis with MS[3], a much faster technique and one that is sensitive and more definitive with regard to post-translational modifications.

In the second strategy for extracting sequence information, the remaining shortened peptide is analyzed. Classically, this "subtractive Edman" employed amino acid analysis, a cumbersome technique requiring highly purified material and therefore prone to error. Understandably, this approach was not competitive to direct analysis of PTH's. However, for analyzing residual peptide, the advantages of MS are overwhelming, so much so that MS analysis of truncated peptides and small proteins is likely to displace most conventional Edman sequencing of these materials. All that is needed are simple, effective, and easily automated ways of generating the required set of truncated peptides, termed a "ladder", wherein the mass differences between adjacent peaks reflects the sequence. With delayed extraction-MALDI-TOF-MS there is sufficient resolution to assign amino acid residues for laddered peptides and proteins up to about 30,000 daltons.

So far, efforts to chemically generate a mass ladder have adapted the standard Edman degradation. In the original Chait-Kent method[4], ladders were generated by including in the coupling medium a small percentage of capping agent (phenylisocyanate) to block a fraction of the peptide to further degradation, i.e., to make the Edman chemistry deliberately inefficient. Obvious problems include: 1) if Lys is present (usually true for peptides from a proteolytic digest), then mixtures of products are created for each step of the ladder, 2) the chemical properties of the capping reagent must be carefully matched to PITC and 3) not create extraneous products (neither of which is true in this case), 4) by eliminating the charge on all amino groups, most peptides are rendered much less sensitive to MS analysis, and 5) byproducts of both sequencing and capping reagents are not volatile and must be removed by liquid washing steps that complicate the processing and risk extractive loss of the peptide(s) being sequenced.

A different reagent with slightly improved properties (trifluoroethylisothiocyanate, more volatile but still producing much non-volatile dialkylthiourea) has been introduced along with a different ploy for creating the truncation set that avoids capping: divide the peptide into aliquots and make serial additions of the parent peptide to the reaction pot so that each further addition is put through one fewer cycle of degradation[5]. While effective at creating an even ladder, this is a huge labor for manual processing of multiple samples and renders automation technically challenging, especially if the peptide is poorly soluble. Another shortcoming is that, in the final mix of truncated peptide, there can be no component representing the starting, undegraded member of the series (either the sidechain of lysine is unreacted or the peptide is shortened by at least one residue). In neither this nor the Chait-Kent method is there any mechanism for distinguishing the isobaric residues isoleucine and leucine.

The underlying chemical basis for the method described here was explored by Levy in the early 1950's. However, under his conditions the process of degradation was inefficient, with both size- and residue-related adverse effects[6]. A re-evaluation of Levy's chemistry in the late 1970's (G. E. Tarr, unpublished in any form) confirmed the inefficiency problem and showed that acidolytic regeneration of the starting peptide was the "side reaction" responsible. In consequence, the method could not compete with the high-efficiency Edman degradation under classical conditions. To my knowledge, the Levy degradation has not been considered for or incorporated into any other method or invention.

Finally, alternative, non-chemical methods for generating mass ladders should be mentioned. Exopeptidases, especially carboxypeptidases Y and P, have been successfully used in conjunction with MS to obtain sequence information on purified peptides and occasionally on mixtures. However, most peptides fail to yield more than a few residues of information, often none at all, because of highly variable reaction rates with different residues and groups of residues. This variability frequently leads to gaps in the sequence as well, as the enzyme rushes through a string of easily removed residues before stalling on the next difficult one. The lack of phase control also makes it impossible to specify the length of the ladder to be generated. These limitations become most extreme when attempting to process mixtures of peptides, as in a proteolytic digest: often only one peptide will show any laddering at all under any particular condition (the rest will be either undigested or completely digested). Furthermore, most digestions require multiple testing and adjustment of conditions to be successful[7].

OBJECTS AND ADVANTAGES

The problems associated with the use of isothiocyanates for the generation of mass ladders are avoided with the alternative derivatizing agent, carbon disulfide ($CS_2$), using the scheme drawn in FIG. 1. For MS analysis, the inefficiency "problem" encountered by Levy and later by Tarr is a virtue: the intrinsic inefficiency means that only one aliquot of the sample is required and no special capping chemistry or serial addition tricks need be applied. Furthermore, the ratio between truncation of the peptide or protein ("cleavage") and regeneration may be controlled for optimal results by choice of reaction conditions. Also, regenerative acidolysis means that both the truncated peptides and starting material bear free amino groups, promoting both sensitivity and ease of interpretation of the associated mass spectrum. Furthermore, all reagents and byproducts are volatile (no analogue of a dialkylthiourea is produced and any product with residual ammonia is decomposed in the acid step) and readily removed under vacuum. The simplicity of the method favors automation. A final advantage of this method is that the bifurcating reaction pathway permits kinetic distinction of isoleucine and leucine.

Further objects and advantages of my invention will become apparent from the ensuing description.

Figure 3:
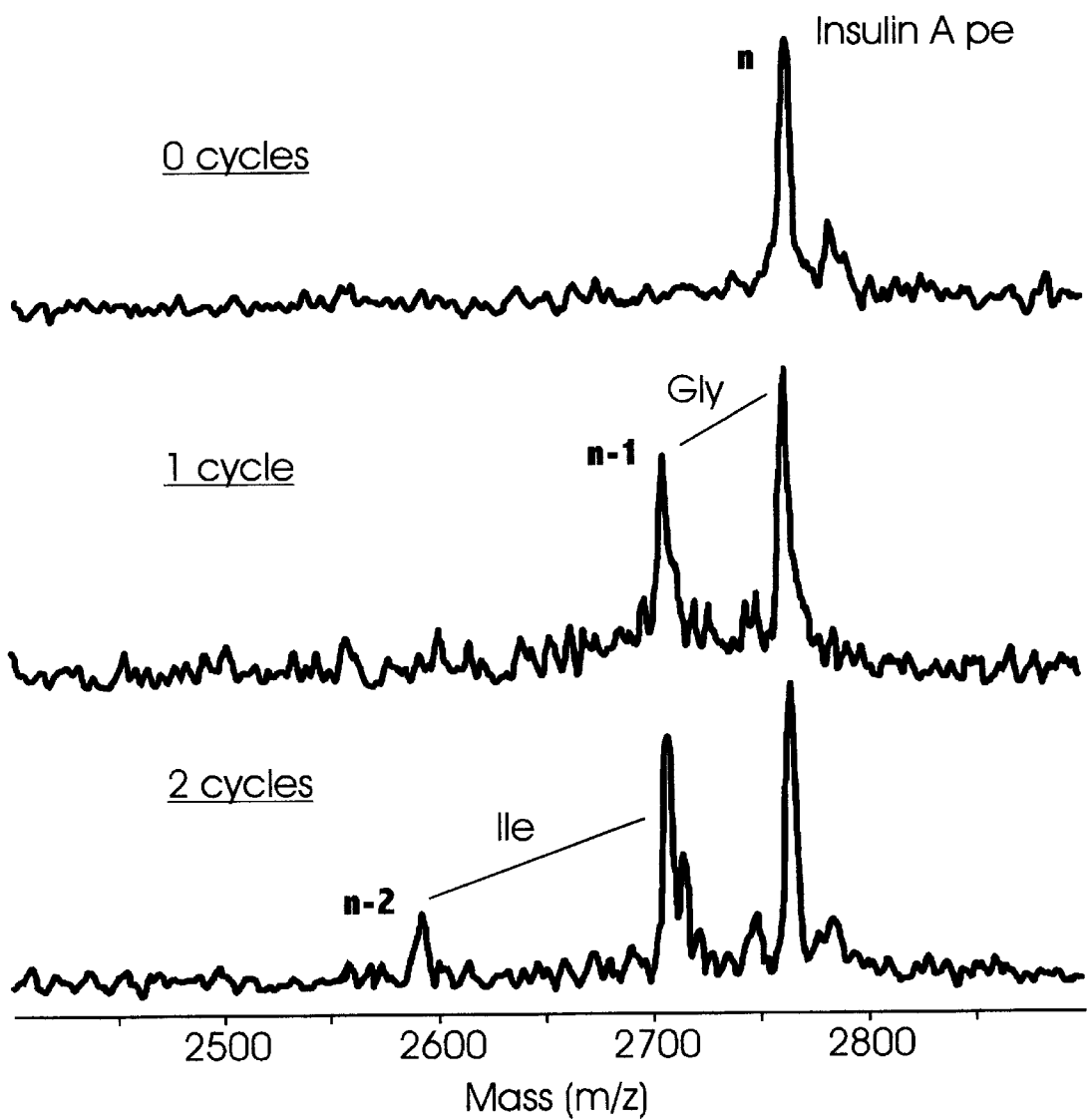

The remaining figures (and tables) support the Description of Invention:

FIG. 3 shows the results of $CS_2$ degradation of S-pyridylethylated insulin A chain.

Figure 4:
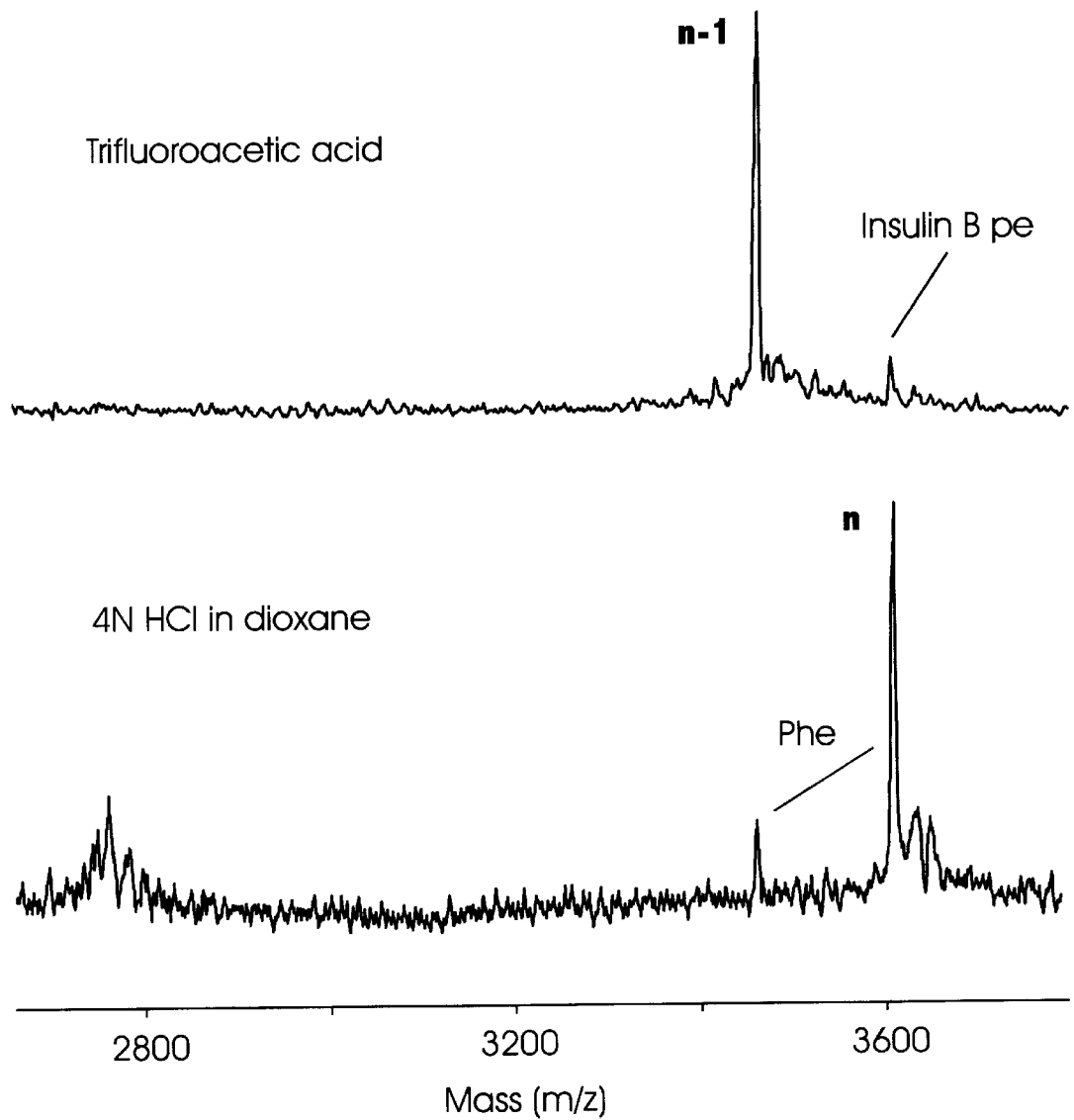

FIG. 4 shows the effect of different acids on the degradation of insulin B chain.

Figure 5:
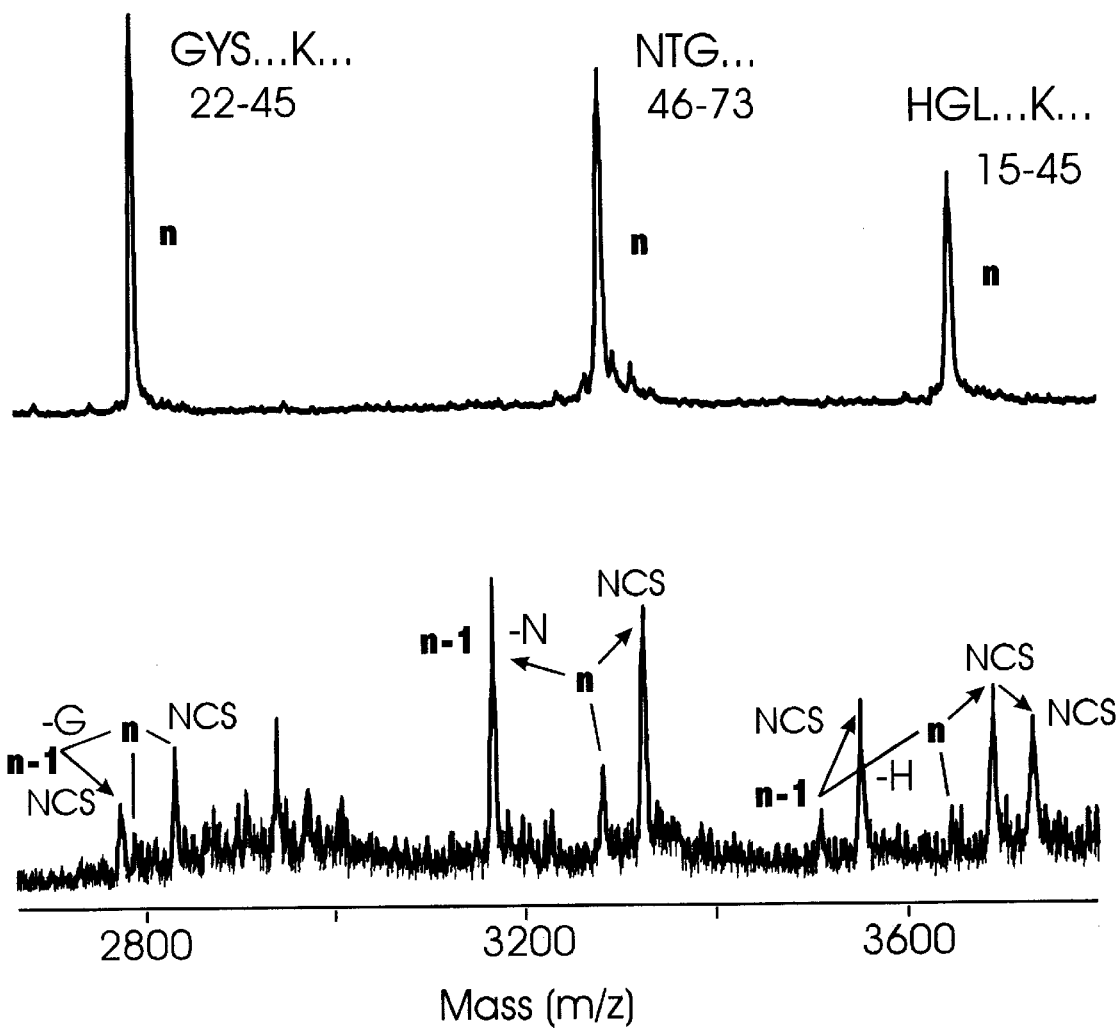

FIG. 5 shows the results of one cycle of degradation applied to an HPLC fraction containing three tryptic peptides from chicken lysozyme.

DESCRIPTION OF INVENTION

The invention herein described comprises 1) a set of chemical reactions to be applied to a peptide or protein or mixture of these materials in order to generate 2) an N-terminal truncation set or sets ("ladders"), and 3) an analytical readout of these ladders by mass spectrometry (MS). None of these components is entirely new. The use of truncation sets and their analysis by mass spectrometry have both been well described in the research literature (see refs 4,5 and 7). The chemistry of carbon disulfide ($CS_2$) and its reaction with primary and secondary amines has also been well studied, especially as part of a sequence of reactions leading to isothiocyanates[8]. The use of $CS_2$ for the sequential degradation of peptides was described in the early 1950's[6,] faulted for the inefficiency of the process, and abandoned. This inefficiency is a virtue rather than a vice when the desired product is a mass ladder, but it is still necessary to reinvestigate the reactions involved in the degradation in order to establish the best conditions. The inventor has been occupied in that research since filing a Provisional Patent Application one year ago and, while the fundamental description stands as disclosed in that document, much detail that was not available at that time may now be added. Also, a serious side-reaction that was not apparent in the initial data was discovered. While this side-reaction was known in another context, there was no reason to believe that it would be a problem here and so was not mentioned in the PPA.

Figure 1:
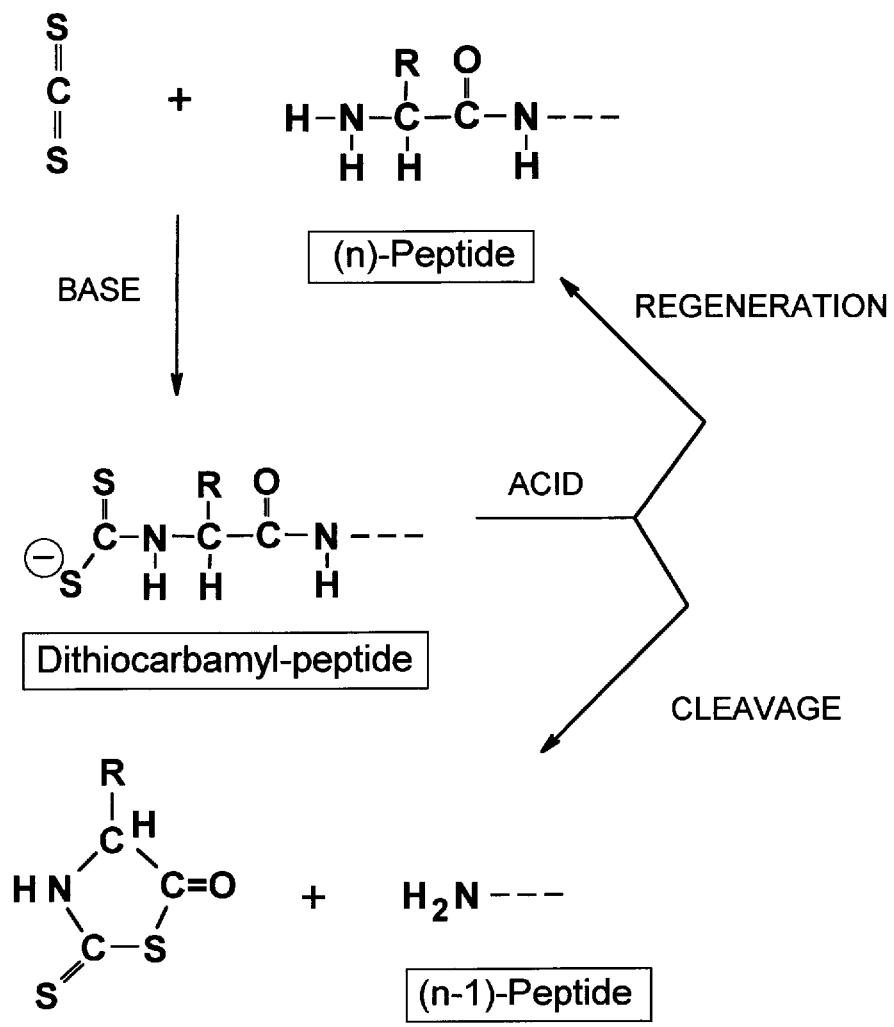
FIG. 1 is a sketch of the chemical reactions that comprise my invention.

The chemical reactions forming the basis of my invention are sketched in FIG. 1. The first step (coupling) shows the reaction under basic conditions of carbon disulfide with the N-terminal amino group of a peptide or protein to produce a dithiocarbamate. The second step (cleavage/regeneration) depicts the results of exposure of this dithiocarbamate to acid, wherein two pathways are followed, one leading to peptide or protein truncated by one amino acid residue, the other to regeneration of the parent peptide or protein. Further application of this two-step degradation leads to further shortening of the original material by two, three, or more amino acid residues according to the number of cycles applied. Thus, a truncation set or "ladder" is produced, which may be conveniently analyzed by mass spectrometry in order to deduce the N-terminal sequence of the peptide or protein. The side-chain amino group of lysine also couples with $CS_2$ but, being incapable of participating in a cyclization, undergoes only regeneration and therefore does not contribute to a change in mass.

The initial data supporting my invention is reproduced from the PPA as FIGS. 3 and 4. To generate this data, about 20 pmol of peptide was dried in a PCR tube, then dissolved in 0.5 $\mu$L water, 3.5 $\mu$L dimethylformamide, and 0.5 $\mu$L triethylamine. Then 2 $\mu$L $CS_2$ was added and the sample vigorously mixed. After 10 min RT the mixture was vacuum dried, 5 $\mu$L trifluoroacetic acid (TFA) was added, and the sample incubated for 5 min at 50° C. (For the lower trace in FIG. 4, 4N HCl in dioxane was substituted for TFA.) After vacuum drying, the sample was dissolved in 2 $\mu$L acetonitrile: 0.1% aq TFA 1:1 and 0.1 $\mu$L was mixed with 1 $\mu$L of 1% $\alpha$-cyano-4-hydroxycinnamic acid for MALDI analysis. The instrument was a PerSeptive Biosystems linear Voyager with Delayed Extraction. As expected from the literature and previous experience, coupling a test peptide with $CS_2$ followed by exposure to acid (conditions given in the legend for FIG. 3) resulted in two products observed by MALDI-TOF-MS—the peptide shortened by one amino acid residue (cleaved) and the intact peptide (regenerated). Two cycles of application of this chemistry resulted in three products—peptide shortened by two residues, peptide shortened by one residue, and intact peptide. As is especially compelling for the large peptide insulin B chain (FIG. 4), no mass change due to application of the $CS_2$ degradation, besides truncation, is observed in the mass spectrum.

Figure 2:
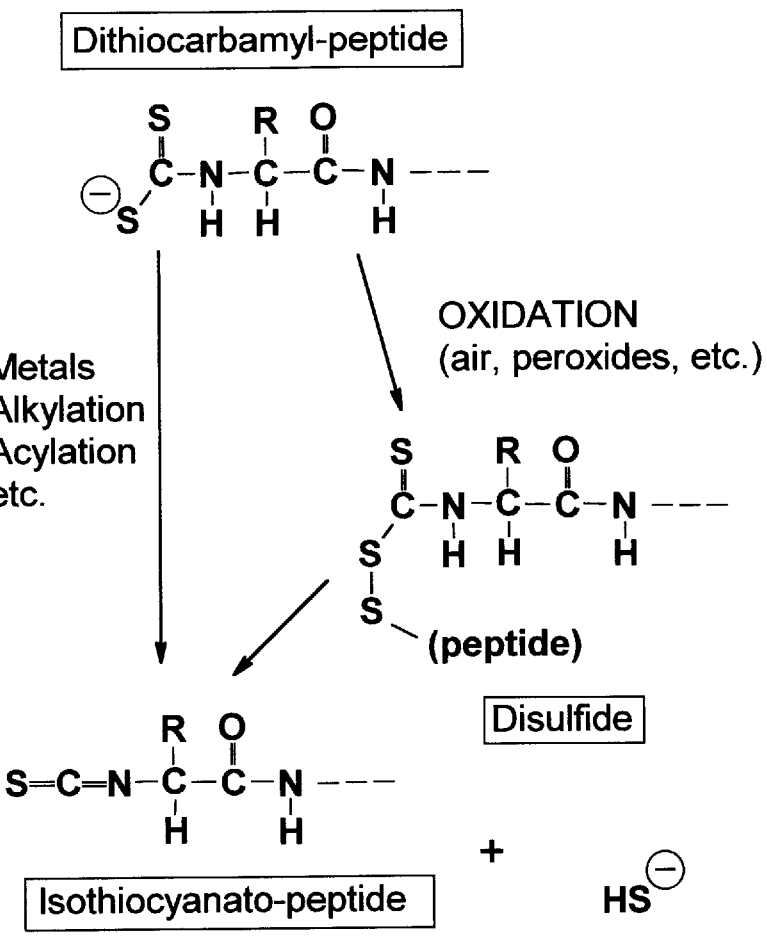
FIG. 2 is a sketch of the side-reaction of dithiocarbamyl-peptide or protein to form an isothiocyanate by elimination of hydrosulfide.

However, it soon became evident that an additional product, not seen at first, was regularly being formed from a variety of other peptides (see FIG. 5). This product had a mass 42 higher than the unprocessed peptide and reacted with primary amines to give adducts with masses consistent with mixed thioureas, i.e., this side-product was the isothiocyanate. An example is shown in FIG. 5: An HPLC fraction containing three tryptic peptides from lysozyme was processed one cycle as described for FIG. 3. MALDI-MS analysis showed a very complex pattern. Peptides and eliminated residues are designated by standard single letter code; "n" and "n−1" are the regenerated and cleaved peptides, respectively; "NCS" indicates isothiocyanate side-products. Note that the two peptides containing lysine (K) generated n−1/NCS productes while the middle peptide, lacking a sidechain that can form an NCS derivative, did not. There are many ways of eliminating hydrosulfide from the dithiocarbamyl-peptide formed by condensation of peptide with CS$_2$, but I had assumed that this elimination required a special activating agent, as described in the literature—heavy metal, alkylating or acylating agent (see ref 8)—and would not happen "spontaneously". (Formation of protein isothiocyanate is noted in the literature on the toxicity of CS$_2$[9], but in vivo conditions seem irrelevant to those of this method.) Evidence at this point suggests that the main mechanism is air oxidation of the dithiocarbamyl-peptide to the disulfide, followed by elimination of the elements of hydrosulfide from one member of the pair (see FIG. 2). However, there appear to be other contributions from trace peroxides in solvents, metals on the walls of tubes and pipettes, and artifacts of analysis, to name a few. And even when the production of NCS-peptide is suppressed, vacuum drying of the coupling medium, in general a necessary prelude to acid cleavage, results in much higher levels of side-product. If the side-reaction proves resistant to complete suppression, known chemistry suggests that any NCS-peptides can be returned to the corresponding dithiocarbamyl-peptides by treatment with excess hydrosulfide, either within each cycle or as a penultimate step at the end of processing. Completely effective scavengers, preservatives, and/or reversal agents or conditions have not been defined experimentally at the time of this disclosure, although there is every confidence they will be found. Finally, an alternative to suppression of the side-reaction to NCS-peptide is exploitation: this side-product can be reacted, either within each cycle or at the end, with reagents bearing fixed positive charges or other MS sensitivity-enhancing groups. (This is a whole field of research unto itself and beyond the scope of the present description.) The number of amino groups in the peptide would be ascertainable as well. The benefits of this variation often may outweigh the advantages of simplicity afforded by the original form of the chemistry.

Catalysis of dithiocarbamylation by tertiary amines has been investigated in detail. As is apparent from the data in Table I,

TABLE I

Catalysis of dithiocarbamylation of Ile—Ser—Ala—dab

| Tert-amine | T$_{1/2}$ (sec) | NCS- (%) | Amine type |
|---|---|---|---|
| A. Effect of various tert-amines | | | |
| Diazabicyclooctane | 34 | 7.1 | Strained diamine |
| Dimethylpiperazine | 90 | 5.1 | Diamine |
| Diazabicycloundecane | 95 | 2.4 | Amidine |
| Tetraethylethylenediamine | 111 | 11.0 | Diamine |
| N-methylpiperidine | 112 | 5.1 | Monoamine |
| Tetramethylpropylenediamine | 117 | 5.6 | Diamine |
| Triethylhexahydrotriazine | 123 | 2.5 | Triamine |
| Dimethylallylamine | 124 | 7.2 | Monoamine |
| Quinuclidine | 128 | 6.9 | Strained monoamine |
| Diisopropylethylamine | 135 | 5.3 | Monoamine |
| Triethylamine | 137 | 5.8 | Monoamine |
| Tetramethylguanidine | 141 | 8.0 | Guanidine |
| N-ethylmorpholine | 222 | 8.6 | Monoamine |

All tests in small glass tubes (6 × 22 mm), 8 uL total volume of methanol plus 12% tert-amine (.5–.8M) and 12% CS$_2$, 16° C. Reaction stopped with 6 uL water, excess CS$_2$ blown off with nitrogen. Immediate analysis by reversed-phase LC on POROS (4.6 × 100 mm), pH 8.5 (40 mM tris), 450 nm, 20° C. Half-lives calculated from normalized recovery of Ile—Ser—Ala—dab.

TABLE I-continued

Catalysis of dithiocarbamylation of Ile—Ser—Ala—dab

| | T$_{1/2}$ (sec) | NCS- (%) | Amine type |
|---|---|---|---|
| B. Effect of various solvents on diazabicyclooctane catalysis | | | |
| Solvent:catalyst[1] 5:2 | | | |
| Methanol | 63 | 6.6 | |
| Ethanol | 48 | 8.1 | |
| 2-Propanol | 50 | 8.2 | |
| Ethylene glycol | 79 | 48.2 | |
| Dimethylformamide | 4 | 5.8 | |
| Dimethylacetamide | 3 | 4.4 | |
| Solvent:catalyst[1] 6:1 | | | |
| Dimethylacetamide | 2 | 7.9 | |
| Dimethylacetamide:water 12:1 | 4 | 4.4 | |
| Dimethylactamide:water 5:1 | 5 | 6.8 | |
| N-methylpyrrolidone | 2 | 8.4 | |

[1]methanol:diazabicyclooctane 4:1 Other conditions as above.

both tert-amine and solvent have marked effects on reaction rate as determined from early kinetics with a chromophore-labeled tripeptide. Only a weak correlation of reaction rate with basicity was apparent (part A), and a somewhat stronger correlation with a diamine structure. Part of the latter effect is probably explained as an increase in equivalent strength—increasing proportion of amine does accelerate the reaction at low concentrations, though the effect is not pronounced at these concentrations. But the effectiveness of the strained diamine diazabicyclooctane appears to be unique. Neither other diamines nor the strained monoamine analogue quinuclidine comes closer than a factor of 3 in efficacy. It must be noted that not only is the reaction much faster with certain tert-amines, but the best catalysts also drive the reaction to completion (data not shown). Reaction in the presence of triethylamine or other less effective catalysts will only approach completion with addition of extra CS$_2$, probably because during prolonged reaction, the initial quantity of this volatile reagent escapes to fill the enclosed space in the reaction chamber.

The solvent used for the coupling reaction has a dramatic effect on reaction rate (Table IB). Non-protic amides afford much faster reaction than alcohols, so fast that sufficiently complete coupling can be achieved in a few seconds. (Note that a small percentage of incomplete coupling would have no significant effect on a method such as this one that relies on intrinsic inefficiency for many of its benefits.) Unfortunately, under current conditions, formamide and acetamide give a more severe production of NCS-peptide on drying than do alcohols. A minor fraction, up to about 15% of the total reaction volume, of water may be added to help solvate a peptide without producing a biphasic mixture; reaction is slowed, but not dramatically so.

Cleavage of the product of the Edman coupling reaction (phenylthiocarbamyl-peptide) requires strong acid. This was found to be less important with dithiocarbamyl-peptides. Even as weak an acid as 90% aqueous acetic gave a half-life (t$_{1/2}$) at room temperature of 35 sec with coupled substance P, based on early kinetics. The much stronger acid TFA gave a t$_{1/2}$ of about 5 sec, with 88% formic acid intermediate in strength and t$_{1/2}$ at 10 sec. Besides reduced acid strength, formic acid is a good choice over TFA because it forms volatile salts with tert-amines and generally yields a favorable ratio of cleavage to regeneration. Table II shows results with a variety of acids. Clearly, this important ratio can be controlled by choice of conditions.

TABLE II

Different cleavage acids effect the ratio of cleavage to regeneration
Cleavage/regeneration for $CS_2$-substance P (Arg—Pro . . . )

| | | |
|---|---|---|
| Trifluoroacetic acid (TFA) | 55° C. | 10.1 |
| Heptafluorobutyric acid | 55° C. | 7.3 |
| Conc HCl | 37° C. | 6.7 |
| 85% $H_3PO_4$ | 55° C. | 6.7 |
| 88% formic acid | 37° C. | 4.3 |
| 1.2N HCl in propanol/water | 37° C. | 4.0 |
| Acetic acid | 55° C. | 0.7 |
| .05% TFA in acetonitrile/water | 22° C. | 0.0 |

Substance P was coupled, aliquoted and cleaved essentially as described in Table III. Analysis with Waters HPLC, Vydac C18 4.6 × 150, .09% TFA, gradient of acetonitrile 23–51% in 8 min, flow 1 mL/min, 22° C., 210 nm.

TABLE III

Distinguishing Ile/Leu: cleavage ratios for $CS_2$—I/L—SAdab

Ratio of cleavage to regeneration (SAdab/I,L—SAdab)

| | Temp: 15° C. | | 36° C. | 48° C. |
|---|---|---|---|---|
| N-terminal residue | 90% aq acetic | 88% aq formic | 90% aqueous trifluoroacetic acid | 88% aq formic |
| Ile— | .09 | .37 | .39 | .37 | .16 |
| Leu— | .32 | 1.04 | .96 | .79 | .47 |

About 1 nmol of the Ile— or Leu— chromophore-labeled Ser—Ala was coupled with $CS_2$ (10 uL ethanol/triethylamine/$CS_2$ 8/1/1 30 min RT), vacuum dried, redissolved in ethanol, aliquoted for the various tests, and redried. Samples were treated for 10–15 min with the acid (about 10 uL) and temperature indicated, redried and analyzed by HPLC. The Waters 625 LC was equipped with a Model 486 detector (set at 540 nm) and a Vydac 90A C18 column 2.1 × 250 mm (30° C., isocratic .1% TFA/27% acetonitrile, flow rate .3 ml/min). Side-product was ignored in the calculations.

A final aspect of the chemistry is the kinetic distinction of the isobaric residues isoleucine (Ile) and leucine (Leu). In other laddering methods, there is no way to discriminate these two amino acid residues. But using this method, it is found that the cleavage to regeneration ratio is distinctly different; Table III shows the results with the chromophore-labeled tripeptide. This difference was also clear with similar analyses of Ile- and Leu-bradykinin on MALDI-TOF-MS, which in turn was consistent with the HPLC analyses of the same material.

REFERENCES

1. P. Edman, A. Henschen 1975 In *Protein Sequence Determination* (S. B. Needleman, ed.), Springer-Verlag, N.Y., 232–279
2. R. M. Hewick, M. W. Hunkapiller, L. E. Hood, W. J. Dreyer 1981 J. Biol. Chem. 256, 7990–7997
3. D. Hess, H. Nika, D. T. Chow, E. J. Bures, H. D. Morrison, R. Aebersold 1995 Anal. Biochem. 224, 373–381
4. B. T. Chait, R. Wang, R. C. Beavis, S. B. H. Kent 1993 Science 262, 89–92
5. M. Bartlet-Jones, W. A. Jeffery, H. F. Hansen, D. J. C. Pappin 1995 In *Techniques in Protein Chemistry VI* (J. W. Crabb, ed.), Academic Press, N.Y., 3–11
6. A. L. Levy 1950 J. Chem Soc. 1950 404 (see discussion in Needleman, ref 1, p. 65)
7. D. H. Patterson, G. E. Tarr, F. E. Regnier, S. A. Martin 1995 Anal Chem 67, 3971–3978
8. L. Drobnica, P. Kristian, J. Augustin 1977 In *The Chemistry of Cyanates and Their Thio Derivatives*, Part 2 (S. Patai, ed.), John Wiley, N.Y., 1003–1221
9. W. M. Valentine, V. Amarnath, D. G. Graham, D. C. Anthony 1992 Chem Res Toxicology 5, 254–262

OPERATION OF INVENTION

The sample of peptide or protein, pure or mixed, must be free enough from extraneous material not to interfere with the chemistry or processing. The quantity required is dependent on the sensitivity of the analytical instrument to be used, the number of cycles desired and the ability to operate the $CS_2$ degradation chemistry at that scale; generally, minimum quantity is expected to be routinely in the low picomole range, but femtomol and sub-finol operation may be possible. All materials that contact the reagents or sample, such as glass or plastic test tubes, pipette tips, tubing, etc., should be free of reactive multivalent metals and oxidants. Reagents and solvents should be the highest purity available.

The results discussed in the previous section define a best mode: An automated instrument that applies this chemistry to many samples at the same time—each added only once at the beginning—on a sheet, plate, probe tips, etc., for an arbitrary number of cycles. The "coupling reagent" ($CS_2$, about 10–20% of the mixed reagent), tertiary amine catalyst (diazabicyclooctane, about 5–10% of the mix), and solvent (dimethylformamide, with or without a small percentage of water, the rest of the mix) are introduced in vapor phase to the reaction chamber held at ambient temperature (about 24° C.). After 10–60 sec coupling agents are removed as vapors by vacuum and/ or gas flow, along with any volatile byproducts. The acid (most often 88% formic acid) and any cosolvent for the "cleavage step" are also introduced in the vapor phase, allowed to react at ambient temperature (1–3 min with formic acid) and removed along with any volatile byproducts at the end of reaction by vacuum and/ or gas flow. As in any chemical processing instrument, provisions for temperature control, inert atmosphere (essential to help suppress side-reaction), and waste collection (with special attention to detoxification of the reagent and byproducts) are included. Alternative catalysts, solvents and temperatures may be used, with any necessary adjustment being made to reaction time. Additional agents to suppress, reverse, or exploit the side-reaction to NCS-peptide may be incorporated into this design within any step or as separate steps. Following this processing, the dried samples are dissolved in a few $\mu L$ of 0.1% TFA in water:acetonitrile 1:1 or other solvent and the ladders analyzed by MALDI-TOF-MS or other MS technique.

An alternative embodiment for the chemical processing is an automated instrument that delivers reagents and solvents in whole or in part as liquids. In this case, peptide and protein samples must be held in place either covalently through acid and base-stable, but reversible, linkage or non-covalently through adsorption to a surface or entrapment within a polymer, such that separation of reagents and byproducts from samples by some combination of drying and liquid extraction is possible. Such an instrument resembles a conventional Edman sequencing machine except for the provision for simultaneous multiple sample processing and the absence of an analytical system for the released amino acid derivatives.

A manual embodiment, such as that used for the research described previously, is to place the sample in a small tube that may be closed (a 6×32 mm glass autosampler tube placed inside a 1.6 mL screw-cap polypropylene tube works well). Reagents and solvents are added by syringe or pipette as liquids at room temperature in the proportions indicated for best mode operation and for the times suggested. Excess reagents, solvents, and byproducts are removed by vacuum drying. Other particular examples of operation that work well enough are described in some of the figures and tables. In all cases, processed samples are dissolved in appropriate solvent and analyzed by MS.

CONCLUSION, RAMIFICATIONS, AND SCOPE OF INVENTION

The chemical method of the invention provides a way to generate N-terminal truncation sets (ladders) of peptides and proteins for analysis by mass spectrometry. The method is rapid, sensitive, simple to apply, can process multiple samples simultaneously, works on all peptides with a free N-terminus, can be applied to pure samples and mixtures of peptides, degrades all peptides in a mixture to the same extent, generates truncated peptides free of other modification, affords control over the number of truncation cycles, results in data that is simple to interpret, and allows the discrimination of isobaric residues. The information obtained can be applied wherever amino acid sequence is helpful, including but not limited to the discovery of new peptides or proteins, identification of known proteins through database searches, and the identification of post-translational and experimental modifications.

While particular catalysts, solvents, temperatures, times, procedures for measuring fluids, containers, and drying procedures have been specified, no restriction on the range of these parameters that may prove useful is implied. Only the coupling reagent carbon disulfide is judged to be unique. The embodiments described are examples of how the invention might best be applied and are not exhaustive or exclusive of other embodiments.

I claim:

1. A method for producing a set of truncated peptides from a peptide or protein for analysis by mass spectrometry, comprising the steps of:

(a) reaction of an N-terminal amino group of said peptide or protein with a reagent carbon disulfide to yield a dithiocarbamyl-peptide or protein, (b) removal of excess reagent and byproducts, (c) treatment of said dithiocarbamyl-peptide or protein with acid, which will:

(1) in part, remove one amino acid residue from the N-terminus of said dithiocarbamyl-peptide or protein, and (2) in part, regenerate said peptide or protein of (a), (d) removal of excess acid and byproducts, (e) repetition of steps (a) through (d) any desired number of times, and (f) analysis of said set of truncated peptides by mass spectrometry.

* * * * *